US011925357B2

(12) United States Patent
Terrazas et al.

(10) Patent No.: US 11,925,357 B2
(45) Date of Patent: Mar. 12, 2024

(54) SYSTEM FOR CONNECTING A MEDICAL IMPLANT TO AN INSERTION AID

(71) Applicant: PFM MEDICAL AG, Cologne (DE)

(72) Inventors: Rodrigo Terrazas, Saarbruecken (DE); Pierre Weitzig, Irrel (DE)

(73) Assignee: PFM MEDICAL AG, Cologne (DE)

( * ) Notice: Subject to any disclaimer, the term of this patent is extended or adjusted under 35 U.S.C. 154(b) by 293 days.

(21) Appl. No.: 17/309,135

(22) PCT Filed: Nov. 7, 2019

(86) PCT No.: PCT/EP2019/080621
§ 371 (c)(1),
(2) Date: Apr. 29, 2021

(87) PCT Pub. No.: WO2020/099248
PCT Pub. Date: May 22, 2020

(65) Prior Publication Data
US 2022/0008081 A1    Jan. 13, 2022

(30) Foreign Application Priority Data
Nov. 14, 2018    (IT) .......................... 102018000010311

(51) Int. Cl.
*A61F 2/82*    (2013.01)
*A61B 17/12*    (2006.01)
(Continued)

(52) U.S. Cl.
CPC ...................... *A61B 17/1214* (2013.01); *A61B 2017/00526* (2013.01); *A61B 2017/12054* (2013.01); *A61B 17/12122* (2013.01)

(58) Field of Classification Search
CPC .......... A61B 17/1214; A61B 17/12122; A61B 17/12145; A61B 2017/00526; A61B 2017/12054
See application file for complete search history.

(56) References Cited

U.S. PATENT DOCUMENTS 5,536,274 A    7/1996 Neuss
6,793,673 B2 *  9/2004 Kowalsky ............. A61F 2/2451
                                                  623/2.36
(Continued)

FOREIGN PATENT DOCUMENTS

DE    4104702    8/1992
DE    19704269   11/1997
(Continued)

OTHER PUBLICATIONS

International Search Report from corresponding PCT Appln. No. PCT/EP2019/080621, dated Jan. 8, 2020.
(Continued)

*Primary Examiner* — Katherine M Rodjom
*Assistant Examiner* — Lindsey R. Rivers
(74) *Attorney, Agent, or Firm* — Grossman, Tucker, Perreault & Pfleger, PLLC

(57) ABSTRACT

A system for connecting a medical implant to an insertion aid, comprising: a medical implant made of a helically wound wire, wherein the wire is formed into a first loop at the proximal end of the medical implant; a cylindrical, hollow insertion aid with a second loop at the distal end of the insertion aid; and a locking wire, which extends through the hollow insertion aid and is relatively movable to the insertion aid; wherein in a first operating state, in which the medical implant is connected to the insertion aid, the second loop of the insertion aid extends through the first loop of the medical implant and the locking wire extends through the second loop of the insertion aid, so that the first loop of the medical implant is arranged between the second loop of the insertion aid and the locking wire; and wherein in a second operating state the locking wire is retracted into the hollow insertion aid and out of the second loop, so that the first loop of the medical implant is no longer connected to the second (Continued)

loop of the insertion aid. A medical implant for such a system.

8 Claims, 2 Drawing Sheets

(51) Int. Cl.
*A61F 2/89* (2013.01)
*A61F 2/95* (2013.01)
*A61F 2/966* (2013.01)
*A61B 17/00* (2006.01)
*A61F 2/915* (2013.01)

(56) References Cited

U.S. PATENT DOCUMENTS

| | | | |
|---|---|---|---|
| 7,166,122 B2* | 1/2007 | Aganon | A61B 17/12145 606/200 |
| 2004/0106946 A1* | 6/2004 | Ferrera | A61B 17/12145 606/200 |
| 2008/0045997 A1 | 2/2008 | Balgobin et al. | |
| 2008/0082176 A1* | 4/2008 | Slazas | A61B 17/12022 623/23.72 |
| 2016/0228127 A1* | 8/2016 | Zhang | A61B 17/12145 |
| 2017/0000632 A1 | 1/2017 | Schaefer | |

FOREIGN PATENT DOCUMENTS

| | | |
|---|---|---|
| EP | 0902651 | 7/2002 |
| EP | 1728477 | 12/2006 |
| WO | 2007/070792 | 6/2007 |
| WO | 2015/078807 | 6/2015 |

OTHER PUBLICATIONS

Written Opinion from corresponding PCT Appln. No. PCT/EP2019/080621, dated Jan. 8, 2020.

* cited by examiner

SYSTEM FOR CONNECTING A MEDICAL IMPLANT TO AN INSERTION AID

FIELD

The present invention relates to a system for connecting a medical implant to an insertion aid. An implant is an artificial device that is implanted into the human or animal body, which remains permanently or temporarily within the human or animal body.

BACKGROUND

An example for a medical implant is a so-called stent, which is inserted into a hollow organ of the human or animal body to keep it open. The stent can be for example a small wire frame of metal or synthetic fibre in a tubular form. Stents are used on the one hand in blood vessels, especially in the coronary vessels, to prevent a repeated occlusion after their expansion. On the other hand, stents are used in the cancer treatment to keep stenosis open after their expansion that are caused by malignant tumours.

Furthermore, medical implants are used in cardiac surgeries, wherein the medical implants are often used to occlude abnormal openings within the heart.

As far as possible, such medical implants are implanted into the human or animal body using a minimal invasive method. During a minimal invasive method an access to a larger blood vessel within the human or animal body is created, via which a catheter is inserted into the human or animal body. Via the blood vessels the catheter is guided to an implantation site. Afterwards the medical implant is transported via the catheter using an insertion aid.

Usually medical implants consist of a memory-shaped material, such that the medical implant unfolds into a predefined shaped after exiting the catheter. The medical implant is thus transported via the catheter to the implantation site using the insertion aid and unfolds into the predetermined shaper after exiting the catheter. After the medical implant has been correctly implanted at the implantation site in the human or animal body the connection between the insertion aid and the medical implant can be released.

Thus, the medical implant must be connected to the insertion aid as secure as possible during the transport through the catheter and at the same time be released easily from the insertion aid after implantation.

The present invention specifically refers to a medical implant made of a helically wound wire. Such medical implants made of helically wound wire can comprise a core wire within the medical implant to adjust the mechanical characteristics, like e.g. stiffness, of the medical implant.

For medical implants without a core wire it is known from the prior art, e.g. DE 41 04 702 A1 or EP 0 902 651 B1, to clamp the medical implant to the insertion aid. This is for example achieved by a widened portion of the insertion aid which is introduced into the proximal end of the medical implant. A disadvantage of such a connection between the medical implant and the insertion aid is that either a high force is necessary to releasing the clamping connection or that there is a risk that the connection is not secure.

Another system for connecting a medical implant without a core wire to an insertion aid is disclosed in WO 2015/078807 A1. The system comprises a first helical connecting member at the proximal end of the medical implant, a second helical connecting member at the distal end of the insertion aid and a locking wire, which in a first operating state locks the first helical connecting member and the second helical connecting member relative to each other. In the first operating state the first helical connecting member and the second helical connecting member at least partially engage each other and the locking wire extends through the first helical connecting member and the second helical connecting member.

For medical implants with a core wire it is known from the prior art, e.g. DE 197 04 269 A1 or EP 0 902 651 A1, to form a loop at the proximal end of the core wire that is attached to the insertion aid. A disadvantage of such a connection between the medical implant and the insertion aid is that the core wire extends out of the medical wire and that the core wire must be additionally securely fixed to the medical implant.

SUMMARY

It is thus an object of the invention to provide a system for connecting a medical implant made of a helically wound wire to an insertion aid, which provides during the implantation of the medical implant into the human or animal body a secure connection between the medical implant and the insertion aid and at the same time enables an easy release of the connection between the medical implant and the insertion aid after implantation of the medical implant. Furthermore, the system should be usable for medical implants with or without a core wire.

According to the invention the object is solved by a System for connecting a medical implant to an insertion aid, comprising:
 a medical implant made of a helically wound wire, wherein the wire is formed into a first loop at the proximal end of the medical implant;
 a cylindrical, hollow insertion aid with a second loop at the distal end of the insertion aid; and
 a locking wire, which extends through the hollow insertion aid and is relatively movable to the insertion aid;
 wherein in a first operating state, in which the medical implant is connected to the insertion aid, the second loop of the insertion aid extends through the first loop of the medical implant and the locking wire extends through the second loop of the insertion aid, so that the first loop of the medical implant is arranged between the second loop of the insertion aid and the locking wire; and
 wherein in a second operating state the locking wire is retracted into the hollow insertion aid and out of the second loop, so that the first loop of the medical implant is no longer connected to the second loop of the insertion aid.

According to the invention the medical implant has a first loop at the proximal end, which is formed by the wire of the medical implant. Since the first loop is formed from the wire of the medical implant, it can be used for medical implants with and without a core wire. Furthermore, there is no need for additional elements that must be connected to the medical implant, with the risk of breaking of the connection. In contrast to a clamping connection the two loops together with the locking wire provide a connection that cannot be accidentally or coincidentally released. Another advantage of the system according to the invention is the easy and cheap manufacturing.

In a variant of the invention the locking wire extends in the first operating state through the second loop of the insertion aid and further into the proximal end of the medical implant. By extending the locking wire into the proximal end of medical implant the region of the connection between the medical implant and the insertion aid is stiffened, which facilitates the insertion and implantation of the medical implant into the human or animal body.

According to a further variant of the invention the first loop at the proximal end of the medical implant is formed by helically winding the wire at the proximal end of the medical implant, forming the first loop by bending the wire and helically winding back the wire between the existing windings, so that the proximal end of the medical implant comprises windings in opposite directions, which are interleaved with each other. Thus, at the proximal end the medical implant has a double helical winding, one winding into the direction of the first loop and one winding back into the direction of the distal end. The two windings are interleaved, so that they built a continuous surface. Due to the interleaving the stiffness of the medical implant at the proximal end is increased, which facilitates the insertion and implantation of the medical implant into the human or animal body. Further, the proximal end of the medical implant has a continuous and smooth surface without any protruding parts.

In a variant of the invention the end of the wire at the proximal end of the medical implant is cut off, so that the end of the wire is flush with the outer surface of the medical implant. This variant corresponds to a medical implant without a core wire. The helically wound wire thus forms a cylindrical hollow structure. The end of the wire is cut off in such a way, that the outer surface of the medical implant is smooth.

In an alternative variant the end of the wire at the proximal end of the medical implant extents into the inner lumen of the medical implant. In this variant the end of the wire of the proximal end of the medical implant preferably at least partially extends through the inner lumen of the medical implant back to the distal end of the medical implant. Once the wire extents into the inner lumen of the medical implant it acts like a core wire. Thus, this variant corresponds to a medical implant with a core wire. This variant has the further advantage that the core wire is made integrally with the medical implant, so that no connection, particularly no pressure connection, between the medical implant and the core wire is necessary. Furthermore, only one piece, namely the wire, must be provided during the manufacturing of the medical implant instead of at least two, namely the wire for the medical implant and the core wire.

According to a variant of the invention at least a part of the wire extending in the inner lumen of the medical implant is physically, particularly mechanically or chemically treated. For example, at least a part of the wire extending in the lumen of the medical implant is rolled or milled. Further, the end of the wire extending from the proximal end to the distal end can be welded to a part of the medical implant, particularly to the distal end of the medical implant. Thereby, the mechanical properties of the medical implant, like different grades of stiffness of the medical implant, can be set.

Advantageously at least one end of the wire is smooth, preferably both ends of the wire, wherein the end of the wire is preferably smoothed by a mechanical and/or chemical treatment, by providing a smooth welding spot/shot at the end of the wire or by providing a blunted tip to the end of the wire.

In an advantageous variant the outer diameter of the medical implant is between 0.6 cm and 1.2 cm, preferably between 0.8 cm and 1.0 cm. The inner diameter of the medical implant in a variant of the invention is between 0.1 cm and 0.7 cm, preferably between 0.3 cm and 0.5 cm.

Further, in a variant of the invention the wire of the medical implant has a diameter between 0.01 cm and 0.04 cm, preferably about 0.025 cm.

In a preferred variant of the invention the stiffness of the medical implant differs along the length of the medical implant. Thereby the medical implant can be adapted e.g. to the medical requirements and/or to the needs of the implantation site. The stiffness of the medical implant can be amended by the length of the backwinding of the wire at the proximal end, the end of the wire extending into the inner lumen of the medical implant, by the physical, particular mechanical or chemical treatment of the wire of the medical implant and/or by the physical properties and the form of the wire.

According to a further variant of the invention the medical implant and/or the wire of the medical implant are mechanically or chemically treated to customize the features of the medical implant, like e.g. the biocompatibility, mechanical characteristics and so on.

The invention further relates to a medical implant for a system according to the invention made of a helically wound wire, wherein the wire is formed into a first loop at the proximal end of the medical implant.

BRIEF DESCRIPTION OF THE DRAWINGS

In the following the invention will be explained with respect to the embodiments shown in the figures. It shows.

DETAILED DESCRIPTION

Figure 1:
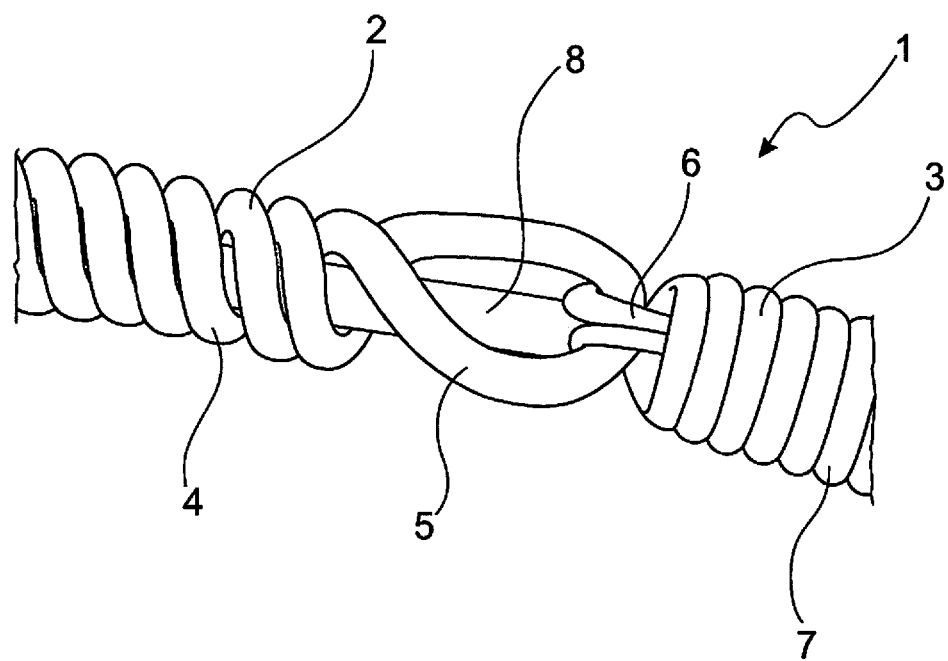
FIG. 1 a perspective view of a first embodiment of an inventive system for connecting a medical implant to an insertion aid.

FIG. 1 shows a perspective view of a first embodiment of an inventive system 1 for connecting a medical implant 1 to an insertion aid 3. In FIG. 1 only the region of the connection between the medical implant 2 and the insertion aid 3 is shown.

The medical implant 2 is made of a helically wound wire 4. Thus, the medical implant 2 has a cylindrical structure, which can be formed to a desired configuration e.g. to occlude an abnormal opening in the human or animal body. The wire 4 of the medical implant 2 is formed into a first loop 5 at the proximal end of the medical implant 2.

The term "proximal" according to the invention refers to the end of the medical implant 2 or of the insertion aid 3 pointing away from the human or animal body and the term "distal" refers to the end of the medical implant 2 or of the insertion aid 3 that points towards the human body.

The insertion aid 3 is cylindrical and hollow and has a second loop 6 at the distal end. The insertion aid 3 is for example made of helically wound wire 7. The second loop 6 is preferably built by a separate wire that extends through the hollow, cylindrical insertion aid 3 and that has a smaller diameter than the wire 4 of the medical implant 4 and wire 7 of the insertion aid 7. Preferably the wire of the second loop 6 is movable relative to the insertion aid 3.

The system 1 further comprises a locking wire 8, which extends through the hollow insertion aid 3 and is movable relative to the insertion aid 3.

FIG. 1 shows the system 1 in a first operating state, in which the medical implant 2 is connected to the insertion aid 3. Therefore, the second loop 6 of the insertion aid 3 extends through the first loop 5 of the medical implant 2 and the locking wire 8 extends through the second loop 6 of the insertion aid 3, so that the first loop 5 of the medical implant 2 is arranged between the second loop 6 of the insertion aid 3 and the locking wire 8.

In a second operating state (not shown) the locking wire 8 is retracted into the hollow insertion aid 3 and out of the second loop 6, so that the first loop 5 of the medical implant 2 is no longer connected to the second loop 6 of the insertion aid 3.

As can be seen from FIG. 1 in the first operating state the locking wire 8 extends through the second loop 6 of the insertion aid 3 and further into the proximal end of the medical implant 2.

The proximal end the medical implant 2 has a double helical winding, one winding into the direction of the first loop 5 and one winding back into the direction of the distal end of the medical implant 2. The two windings are interleaved, so that they built a continuous surface. For example, the first loop 5 at the proximal end of the medical implant 2 is formed by helically winding the wire 4 at the proximal end of the medical implant 2, forming the first loop 5 by bending the wire 4 and helically winding back the wire 4 between the existing windings, so that the proximal end of the medical implant 2 comprises windings extending in opposite directions, which are interleaved with each other.

Alternatively, the first loop 5 at the proximal end of the medical implant 2 can be formed by spacing the helical windings of the wire 4 at the proximal end of the medical implant 2, forming the first loop 5 by bending the wire 4 and helically winding back the wire 4 into the spacings, so that the outer surface of the proximal end of the medical implant 2 is closed.

The end of the wire 4 at the proximal end of the medical implant 2 is cut off, so that the end of the wire 4 is flush with the outer surface of the medical implant 2, to create a medical implant 2 without a core wire. Alternatively, the end of the wire 4 at the proximal end of the medical implant 2 extents into the inner lumen of the medical implant 2 to create a medical implant 2 with a core wire. In this alternative variant the end of the wire 4 of the proximal end of the medical implant 2 at least partially extends through the inner lumen of the medical implant 2 back to the distal end of the medical implant 2.

Advantageously at least a part of the wire 4 extending in the inner lumen of the medical implant 2 is physically, particularly mechanically or chemically treated. For example, at least a part of the wire 4 extending in the lumen of the medical implant 2 is rolled or milled. Further, the end of the wire 4 extending from the proximal end to the distal end can be welded to a part of the medical implant 2, particularly to the distal end of the medical implant 2. Thereby, the mechanical properties of the medical implant 2, like different grades of stiffness of the medical implant 2, can be set.

Preferably, at least one end of the wire 4 is smooth, preferably both ends of the wire 4, wherein the end of the wire 4 is preferably smoothed by a mechanical and/or chemical treatment, by providing a smooth welding sport/shot at the end of the wire 4 or by providing a blunted tip to the end of the wire 4.

The outer diameter of the medical implant 2 is for example between 0.6 cm and 1.2 cm, preferably between 0.8 cm and 1.0 cm and the inner diameter of the medical implant 2, thus the diameter of the inner lumen of the medical implant 2, is for example between 0.1 cm and 0.7 cm, preferably between 0.3 cm and 0.5 cm. The wire 4 of the medical implant 2 has for example a diameter between 0.01 cm and 0.04 cm, preferably about 0.025 cm.

The stiffness of the medical implant 2 can differ along the length of the medical implant 2, for example due to the double winding at the proximal end, the locking wire 8 extending into the proximal end of the medical implant 2 and/or the wire 4 extending into the inner lumen of the medical implant 2 as a core wire. The stiffness of the medical implant 2 can be amended by the length of the backwinding of the wire 4 at the proximal end, the end of the wire 4 extending into the inner lumen of the medical implant 2, by the physical, particular mechanical or chemical treatment of the wire 4 of the medical implant 2 and/or by the physical properties and the form of the wire 4.

Furthermore, the medical implant 2 and/or the wire 4 of the medical implant 2 can be mechanically or chemically treated to customize the features of the medical implant 2, like e.g. the biocompatibility, mechanical characteristics and so on.

Figure 2:
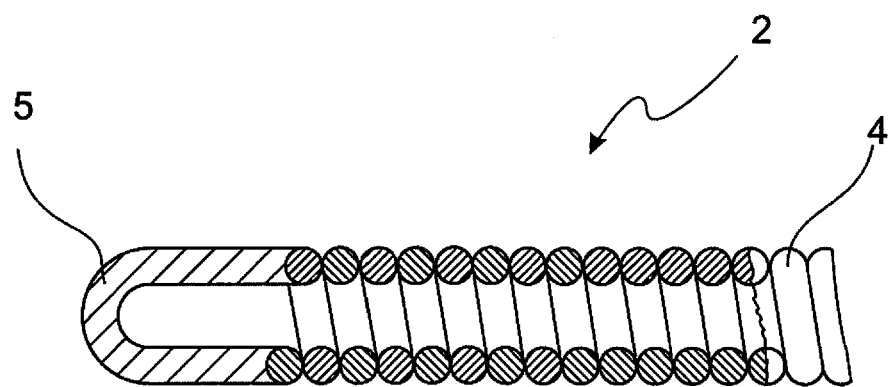
FIG. 2 a cross-sectional view of a second embodiment of an inventive system comprising a medical implant without a core wire.

FIG. 2 shows a cross-sectional view of a medical implant 2 of a system 1 for connecting the medical implant 2 to an insertion aid 3. The medical implant 2 is made of a helically wound wire 4. At the proximal end of the medical implant 2 the wire 4 is formed into a first loop 5.

The first loop 5 at the proximal end of the medical implant 2 is formed by helically winding the wire 4 at the proximal end of the medical implant 2, forming the first loop 5 by bending the wire 4 and helically winding back the wire 4 between the existing windings, so that the proximal end of the medical implant 2 comprises windings extending in opposite directions, which are interleaved with each other. The different winding directions of the wire 4 at the proximal end of the medical implant 2 is illustrated in FIG. 2 by the different directions of the hatching.

The end of the wire 4 at the proximal end of the medical implant 2 is cut off in such a way, that the wire 4 is flush with the outer surface of the medical implant 2. Thus, no parts of the wire 4 extend outside of the medical implant 2 or into the medical implant 2. This results in medical implant 2 with a smooth outer surface and an inner lumen extending from the proximal end to the distal end. Advantageously the end of the wire 4 is smooth, wherein the end of the wire 4 is preferably smoothed by a mechanical and/or chemical treatment, by providing a smooth welding spot/shot at the end of the wire 4 or by providing a blunted tip to the end of the wire 4.

Thus, FIG. 2 shows a medical implant 2 without a core wire, having a generally hollow cylindrical form.

The outer diameter of the medical implant 2 is for example between 0.6 cm and 1.2 cm, preferably between 0.8 cm and 1.0 cm and the inner diameter of the medical implant 2 is for example between 0.1 cm and 0.7 cm, preferably between 0.3 cm and 0.5 cm. The wire 4 of the medical implant 2 has for example a diameter between 0.01 cm and 0.04 cm, preferably about 0.025 cm.

According to a variant of the invention the stiffness of the medical implant 2 can differ along the length of the medical implant 2. Furthermore, the medical implant 2 and/or the wire 4 of the medical implant 2 can be mechanically or chemically treated to customize the features of the medical implant 2, like e.g. the biocompatibility, mechanical characteristics and so on.

As explained with respect to FIG. 1 the system 1 for connecting the medical implant 2 to the insertion aid 3 further comprises the insertion aid 3, which is cylindrical and hollow with a second loop 6 at the distal end of the insertion aid 3 and a locking wire 8, which extends through the hollow insertion aid 3 and is relatively movable to the insertion aid 3.

In a first operating state, in which the medical implant 2 is connected to the insertion aid 3, the second loop 6 of the insertion aid 3 extends through the first loop 5 of the medical implant 2 and the locking wire 8 extends through the second loop 6 of the insertion aid 3, so that the first loop 5 of the medical implant 2 is arranged between the second loop 6 of the insertion aid 3 and the locking wire 8.

In a second operating state the locking wire 8 is retracted into the hollow insertion aid 3 and out of the second loop 6, so that the first loop 5 of the medical implant 2 is no longer connected to the second loop 6 of the insertion aid 3.

Preferably, in the first operating state the locking wire 8 extends through the second loop 6 of the insertion aid 3 and further into the proximal end of the medical implant 2.

Figure 3:
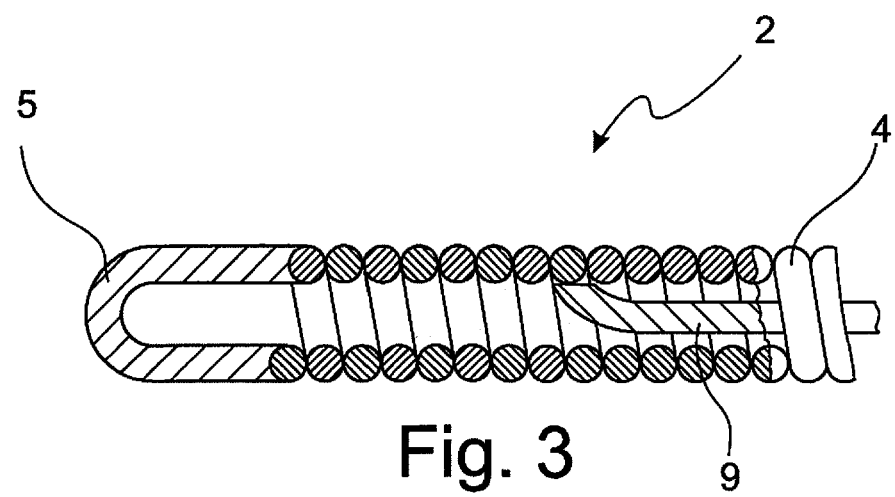
FIG. 3 a cross-sectional view of a third embodiment of an inventive system comprising a medical implant with a core wire.

The embodiment shown in FIG. 3 differs from the embodiment shown in FIG. 2 in that the end of the wire 4 at the proximal end of the medical implant 2 extents into the inner lumen of the medical implant 2. The end of the wire 4 of the proximal end of the medical implant 2 at least partially extends through the inner lumen of the medical implant 2 back to the distal end of the medical implant 2. The end of the wire 4 extending back to the distal end of the medical implant 2 can be welded to the distal end of the medical implant 2.

Once the wire 4 extents into the inner lumen of the medical implant 2 it acts like a core wire 9. Thus, FIG. 3 shows a medical implant 2 with a core wire 9. This embodiment has the further advantage that the core wire 9 is made integrally with the medical implant 2, so that no connection between the medical implant 2 and the core wire 9 is necessary. Furthermore, only one piece, namely the wire 4, must be provided during the manufacturing of the medical implant 2 instead of at least two, namely the wire 4 for the medical implant 2 and the core wire 9.

All other features explained above with respect to the embodiments shown FIG. 1 and or FIG. 2 also apply to the embodiment shown in FIG. 3.

LIST OF REFERENCE NUMBERS

1 system
2 medical implant
3 insertion aid
4 wire (medical implant)
5 first loop
6 second loop
7 wire (insertion aid)
8 locking wire
9 core wire

What is claimed is:

1. A system for connecting a medical implant to an insertion aid, comprising:
   a medical implant made of a helically wound wire, wherein the wire is formed into a first loop at the proximal end of the medical implant;
   a cylindrical, hollow insertion aid with a second loop at the distal end of the insertion aid; and
   a locking wire, which extends through the hollow insertion aid and is relatively movable to the insertion aid;
   wherein, in a first operating state, in which the medical implant is connected to the insertion aid, the second loop of the insertion aid extends through the first loop of the medical implant and the locking wire extends through the second loop of the insertion aid, so that the first loop of the medical implant is arranged between the second loop of the insertion aid and the locking wire;
   wherein, in a second operating state the locking wire is retracted into the hollow insertion aid and out of the second loop, so that the first loop of the medical implant is no longer connected to the second loop of the insertion aid; and
   wherein the medical implant has a double helical winding at the proximal end, one winding into the direction of the first loop and one winding back into the direction of the distal end, which are interleaved to build a continuous surface.

2. The system according to claim 1, wherein in the first operating state the locking wire extends through the second loop of the insertion aid and further into the proximal end of the medical implant.

3. The system according to claim 1, wherein at least one end of the medical implant wire is smooth, wherein the end of the medical implant wire is smoothed by at least one of providing a smooth welding spot at the end of the medical implant wire or by providing a blunted tip to the end of the medical implant wire.

4. The system according to claim 3, wherein the end of the medical implant wire is smoothed by providing the smooth welding spot at the end of the medical implant wire.

5. The system according to claim 3, wherein the end of the medical implant wire is smoothed by providing the blunted tip to the end of the medical implant wire.

6. The system according to claim 1, wherein the wire of the medical implant is at least one of mechanically or chemically treated to amend one or more features of the medical implant.

7. The system according to claim 6, wherein the wire of the medical implant is at least one of mechanically or chemically treated to amend biocompatibility of the medical implant.

8. The system according to claim 6, wherein the wire of the medical implant is at least one of mechanically or chemically treated to amend mechanical characteristics of the medical implant.

\* \* \* \* \*